United States Patent
Kennedy

(10) Patent No.: US 6,190,306 B1
(45) Date of Patent: Feb. 20, 2001

(54) CAPACITIVE INPUT TRANSDUCER FOR MIDDLE EAR SENSING

(75) Inventor: Joel A. Kennedy, Arden Hills, MN (US)

(73) Assignee: St. Croix Medical, Inc., Minneapolis, MN (US)

( * ) Notice: Under 35 U.S.C. 154(b), the term of this patent shall be extended for 0 days.

(21) Appl. No.: 09/375,886

(22) Filed: Aug. 17, 1999

Related U.S. Application Data

(63) Continuation of application No. 08/907,384, filed on Aug. 7, 1997, now Pat. No. 5,954,628.

(51) Int. Cl.$^7$ .................................................. H04R 25/00
(52) U.S. Cl. ................................. 600/25; 607/55; 607/57
(58) Field of Search ................................. 600/25; 607/55, 607/56, 57; 181/129, 130, 131, 132, 133, 134, 135

(56) References Cited

U.S. PATENT DOCUMENTS

| | | | |
|---|---|---|---|
| 4,840,178 | * | 6/1989 | Heide et al. ........................... 600/25 |
| 4,957,478 | * | 9/1990 | Maniglia .............................. 600/25 |
| 5,015,224 | * | 5/1991 | Maniglia .............................. 600/25 |
| 5,498,226 | * | 3/1996 | Lenkauskas ............................ 600/25 |
| 5,531,787 | * | 7/1996 | Lesinski et al. ....................... 623/10 |
| 5,558,618 | * | 9/1996 | Maniglia .............................. 600/25 |

* cited by examiner

Primary Examiner—Cary O'Connor
Assistant Examiner—Charles Marmor, II
(74) Attorney, Agent, or Firm—Fredrikson & Byron, P.A.

(57) ABSTRACT

A hearing assistance system senses sound vibrations of an auditory element in the middle ear and provides a stimulus to an auditory sensory element. The vibrations are received through the tympanic membrane, and sensed at the tympanic membrane, malleus, incus, or other auditory element. A capacitive sensor is mechanically or magnetically coupled to a vibrating auditory element, such as the malleus, and time-varying capacitance values resulting from the vibrations are detected. One embodiment allows pivotable mechanical coupling of the capacitive sensor to at least one of the auditory element and a carrier secured within the middle ear. A resulting electrical output signal is provided to the output stimulator for assisting hearing.

30 Claims, 7 Drawing Sheets

CAPACITIVE INPUT TRANSDUCER FOR MIDDLE EAR SENSING

CROSS REFERENCE TO RELATED APPLICATIONS

This is a continuation of application Ser. No. 08/907,384 filed Aug. 7, 1997 now U.S. Pat. No. 5,954,628.

U.S. patent application Ser. No. 08/907,384 is related to, commonly assigned U.S. patent application "MIDDLE EAR VIBRATION SENSOR USING MULTIPLE TRANSDUCERS," Ser. No. 08/908,236, filed on even date herewith, which disclosure is herein incorporated by reference. This application is also related to, commonly assigned U.S. patent application Ser. No. 08/693,454, which disclosure is herein incorporated by reference.

THE FIELD OF THE INVENTION

This invention relates generally to at least partially implantable hearing assistance systems, and more particularly to the sensing of sound vibrations in the middle ear.

BACKGROUND

Some types of partial middle ear implantable (P-MEI), total middle ear implantable (T-MEI), cochlear implant, or other hearing assistance systems utilize components disposed within the middle ear or inner ear regions. Such components may include an input transducer for receiving sound vibrations or an output stimulator for providing mechanical or electrical output stimuli corresponding to the received sound vibrations.

An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus bone in the patient's middle ear. The malleus vibrates in response to sounds received at the patient's tympanic membrane (eardrum). The piezoelectric input transducer transduces mechanical energy of malleus vibrations into an electrical signal, which is amplified and further processed by an electronics unit. A resulting electrical signal is provided to an electrical-to-mechanical piezoelectric output transducer that generates a mechanical vibration coupled to an element of the ossicular chain or to the oval window or round window. In the '366 patent, the ossicular chain is interrupted by removal of the incus. Removal of the incus prevents the mechanical vibrations delivered by the piezoelectric output transducer from mechanically feeding back to the piezoelectric input transducer.

Another example of such a device is disclosed in U.S. Pat. No. 5,554,096 issued to G. R. Ball on Sep. 10, 1996. In the '096 patent, an external transducer senses sound. A resulting electrical signal is processed and provided to a subcutaneous electromagnetic transducer. In the '096 patent, the electromagnetic transducer is used for vibrating an ossicle.

Another example of such a device is disclosed in U.S. Pat. No. 5,558,618 issued to A. J. Maniglia on Sep. 24, 1996. In the '618 patent, acoustic signals are transduced into electrical signals by external means. A resulting electrical signal is provided to actuate an electromagnet for assisting hearing.

Hearing assistance systems that use piezoelectric input transducers to sense sounds through corresponding ossicular vibrations face numerous difficulties. For example, the bandwidth of the piezoelectric input transducer may not accommodate the full frequency band between 250 Hertz and 5 kilohertz needed for good speech comprehension. Piezoelectric input transducers also typically suffer from a highly nonlinear frequency response due to a resonance frequency in or near the audio frequency range. Piezoelectric input transducers can be quite fragile. In addition, a piezoelectric input transducer typically requires rigid mechanical contact with the auditory element, which results in a mechanical loading that can diminish the gain and frequency sensitivity of the sensed mechanical sound vibrations.

For the reasons stated above, and for other reasons stated below which will become apparent to those skilled in the art upon reading and understanding the present specification, there is a need in the art for sensing middle ear sound vibrations through input transducers that do not have the above-described limitations of piezoelectric input transducers.

SUMMARY

The present invention provides a hearing assistance system that includes non-piezoelectric input sensors for transducing vibrations in the middle ear into electrical signals. One embodiment of the invention includes a sensor for transducing mechanical sound vibrations in a middle ear into an electrical input signal. The sensor includes a capacitor having a first portion that is coupled (e.g., mechanically, magnetically, or otherwise) to an auditory element for receiving the vibrations and changing a capacitance value of the capacitor in response thereto.

According to one aspect of the invention, the sensor may be pivotably coupled to at least one of the auditory element and a carrier secured in the middle ear. Another embodiment includes middle-ear implantable hearing assistance system comprising a capacitive sensor, coupled to an auditory element for receiving vibrations and varying a capacitance value in response thereto. An amplifier is electrically coupled to the capacitive sensor for amplifying a signal resulting from the varying capacitance value. An output stimulator receives a signal based on the varying capacitance value, and provides a resulting stimulus to an auditory element.

The invention also provides a method of transducing a mechanical vibration of an auditory element into at least one electrical signal. A capacitive sensor is coupled to the auditory element for receiving the vibrations, thereby resulting in capacitance variations. The capacitance variations are sensed. An electrical signal is provided in response to the sensed capacitance variations. In one embodiment, the hearing assistance system includes an external programmer for adjusting hearing assistance parameters in a hearing assistance device and for data transmission from the hearing assistance device to the programmer, such as for parameter verification or diagnostic purposes.

Thus, the present invention provides an alternative to piezoelectric input transducers, which have limited and nonlinear frequency characteristics, potential reliability problems associated with their durability, and mechanical loading that can diminish the gain and frequency sensitivity of the sensed mechanical sound vibrations.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views.

The teachings of the present invention disclose a hearing assistance system for sensing mechanical vibrations of an auditory element that avoids the above-described limitations of piezoelectric input transducers. The invention is capable of use as or with a middle ear implantable hearing system such as a partial middle ear implantable (P-MEI), total middle ear implantable (T-MEI), cochlear implant, or other hearing system. A P-MEI or T-MEI hearing system assists the human auditory system in converting acoustic energy contained within sound waves into electrochemical signals delivered to the brain and interpreted as sound.

Figure 1:
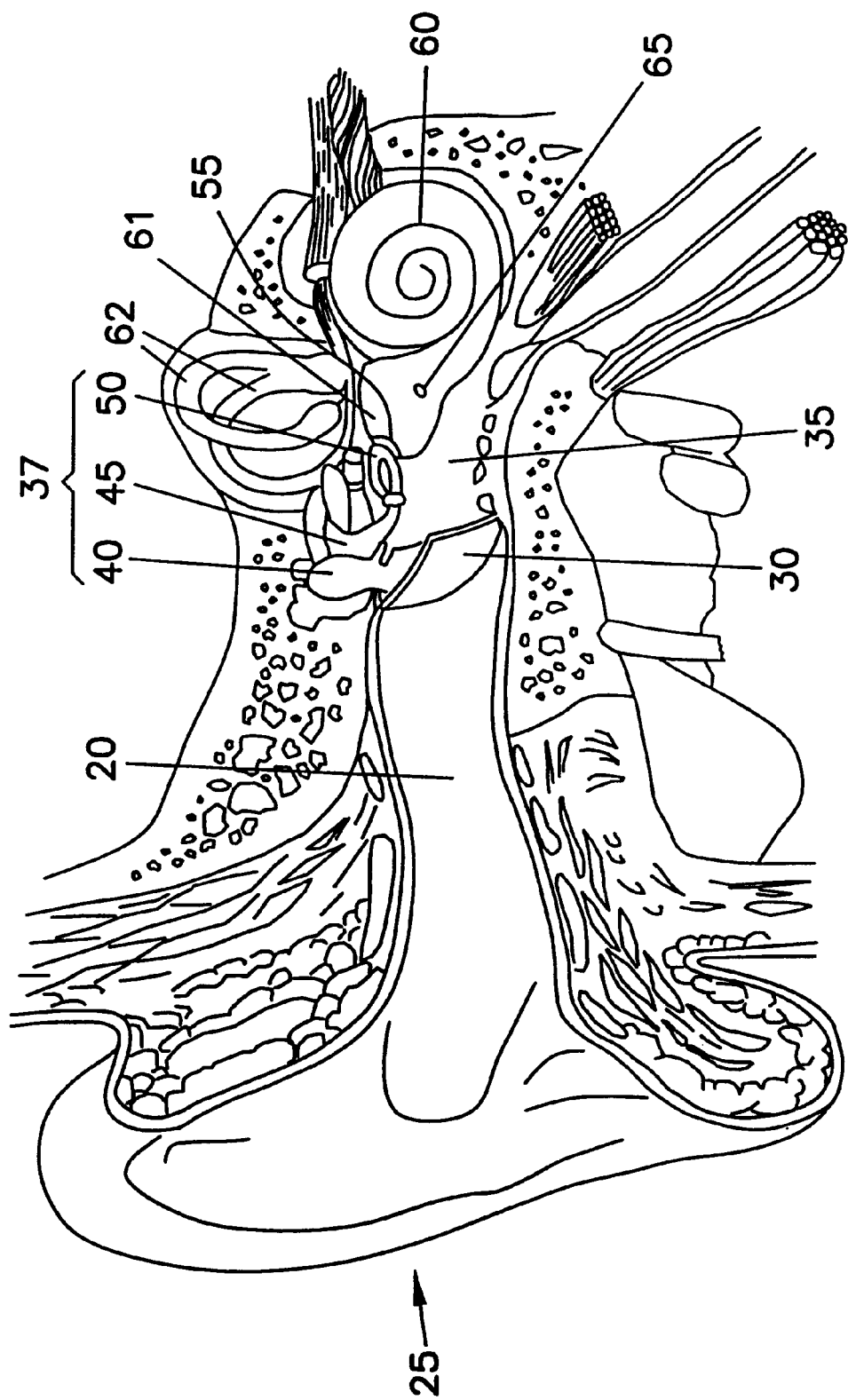
FIG. 1 illustrates generally a human auditory system.

FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three ossicles: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea 60 is referred to as sensorineural hearing loss. Hearing loss due to an inability to conduct mechanical vibrations through the middle ear 35 is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing systems have also been developed, utilizing various approaches to compensate for hearing disorders. For example, cochlear implant techniques implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing systems have been developed to aid patients without an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow coupling of the mechanical vibrations thereto. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer. As described above, piezoelectric input transducers have certain limitations, including with respect to frequency response, durability, and mechanical loading of the sensed auditory element. As described below, the teachings of the present invention disclose a hearing assistance system for sensing mechanical vibrations of an auditory element that avoids such limitations. For implantation of hearing aid components, an access hole 85 is created in a region of the temporal bone known as the mastoid 80. An incision is made in the skin covering the mastoid 80, and an underlying access hole is created through the mastoid 80 allowing external access to the middle ear 35. The access hole 85 is located approximately posterior and superior to the external auditory canal 20.

Figure 2:
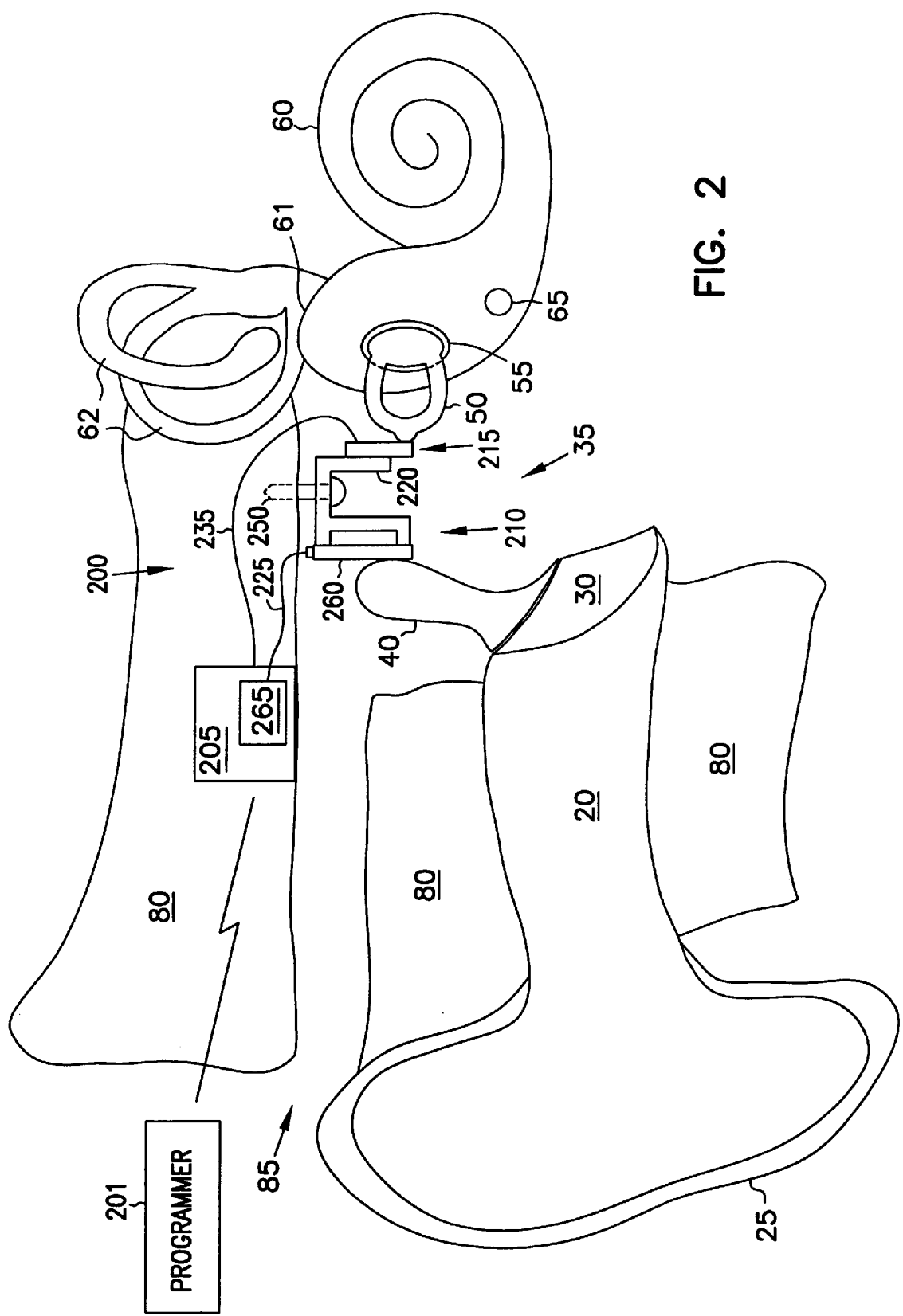
FIG. 2 is a schematic/block diagram illustrating generally one embodiment of a hearing assistance system according to the present invention, including a capacitive input sensor.

FIG. 2 is a schematic/block diagram illustrating generally one embodiment of a hearing assistance system according to one embodiment of the present invention. This embodiment includes hearing assistance device 200, which is implanted in the middle ear 35 and optionally includes portions implanted in the mastoid 80 portion of the temporal bone. In this embodiment, incus 45 is removed. However, such removal of incus 45 is not required to practice the invention. Hearing assistance device 200 includes electronics unit 205, an input sensor 210, and an output stimulator 215. A carrier 220 is provided, such as for mounting portions of input sensor 210 and output stimulator 215. Though a unitary carrier 220 is shown, input sensor 210 and output stimulator 215 could also be affixed by separate carriers or any other suitable means.

The hearing assistance system also includes an external (i.e., not implanted) programmer 201, which is communicatively coupled to an external or implantable portion of hearing assistance device 200. Programmer 201 includes hand-held, desktop, or a combination of hand-held and desktop embodiments, for use by a physician or the patient in which hearing assistance device 200 is implanted.

In one embodiment, each of programmer 201 and hearing assistance device 200 include an inductive element, such as a coil, for inductively-coupled bi-directional transdermal communication between programmer 201 and hearing assistance device 200. Inductive coupling is just one way to communicatively couple programmer 201 and hearing assistance device 200. Any other suitable technique of communicatively coupling programmer 201 and hearing assistance device 200 may also be used.

In one embodiment, such communication includes programming of hearing assistance device 200 by programmer 201 for adjusting hearing assistance parameters in hearing assistance device 200, and also provides data transmission from hearing assistance device 200 to programmer 201, such as for parameter verification or diagnostic purposes. Programmable parameters include, but are not limited to: on/off, standby mode, type of noise filtering for a particular sound environment, frequency response, volume, delivery of a test stimulus on command, and any other programmable parameter.

Input sensor 210 senses the mechanical sound vibrations of an auditory element, and provides a resulting electrical input signal in response thereto. In the embodiment of FIG. 2, malleus 40 is illustrated, by way of example, as the auditory element from which vibrations are sensed, but other auditory elements could also be used, including, but not limited to tympanic membrane 30, incus 45 or other ossicle, or any prosthetic auditory element serving a similar function. Input sensor 210 provides the resulting electrical input signal, such as through one or more lead wires at node 225, to electronics unit 205. Electronics unit 205 receives the input signal that is based on a changing capacitance resulting from the sensed vibrations of the auditory element. Electronics unit 205 provides amplification, filtering, or other signal processing of the input signal, and provides a resulting electrical output signal, such as through one or more lead wires, illustrated generally by node 235, to output stimulator 215. Output stimulator 215 provides mechanical (e.g., vibratory) or electrical (e.g., single or multichannel cochlear implant pulses) stimulation of the inner ear. In the embodiment of FIG. 2, for example, output stimulator 215 transmits mechanical vibrations to oval window 55 of cochlea 60 through stapes 50.

In the embodiment of FIG. 2, a capacitive sensor (capacitor) 260 is mechanically coupled to an auditory element, such as malleus 40, for receiving vibrations. In FIG. 2, a portion of capacitor 260 is mechanically coupled to malleus 40, such as by direct contact, adhesive coupling, or using intermediate rigid coupling elements (e.g., wires or rods). The vibrations of malleus 40 are transmitted to capacitor 260. Another portion of capacitor 260 is secured in a fixed-position with respect to the vibrating auditory element, such as by carrier 220, which is secured by bone screw 250 to a portion of the temporal bone within middle ear 35, or otherwise. As a result of the vibrations, the capacitance value of capacitor 260 varies in response to variations in the spacing between its first and second capacitor electrodes. Variations in the capacitance value of capacitor 260 are detected by an interface circuit 265 in electronics unit 205.

For example, in one embodiment, variations in the capacitance value of capacitor 260 produce an electrical input signal between the first and second capacitor electrodes. The electrical input signal is coupled to electronics unit 205 through separate lead wires 225a and 225b, which are illustrated generally by node 225. Thus, vibrations of the auditory element produce variations in the capacitance value of capacitor 600, resulting in a time-varying electrical input signal that is detected and amplified by interface circuit 265 in electronics unit 205, as described below.

Interface circuit 265 detects the electrical input signal provided by variations in the capacitance value of capacitor 260. Interface circuit 265 provides buffering and amplification so that the electrical input signal can be further processed by electronics unit 205, and an amplified electrical output signal provided to output stimulator 215.

In one embodiment, interface circuit 265 uses voltage amplification to detect voltage variations, $\Delta V$, corresponding to the capacitance variations, $\Delta C$, of capacitor 260 while the charge Q on capacitor 260 is held constant (i.e., $\Delta V = Q/(\Delta C)$). One skilled in the art will appreciate that many high-input impedance voltage amplification techniques that are known in the art will provide suitable voltage amplification and buffering for capacitor 260. In one such embodiment, a dc bias voltage $V_{DC}$ is also provided across capacitor 260, as described below.

In another embodiment, interface circuit 265 uses charge amplification to detect charge variations, $\Delta Q$, corresponding to the capacitance variations, $\Delta C$, of capacitor 260 while the voltage V across capacitor 260 is held constant (i.e., $\Delta Q = (\Delta C)V$). In one such embodiment, a dc bias voltage $V_{DC}$ is also provided across capacitor 260, as described below.

Figure 3:
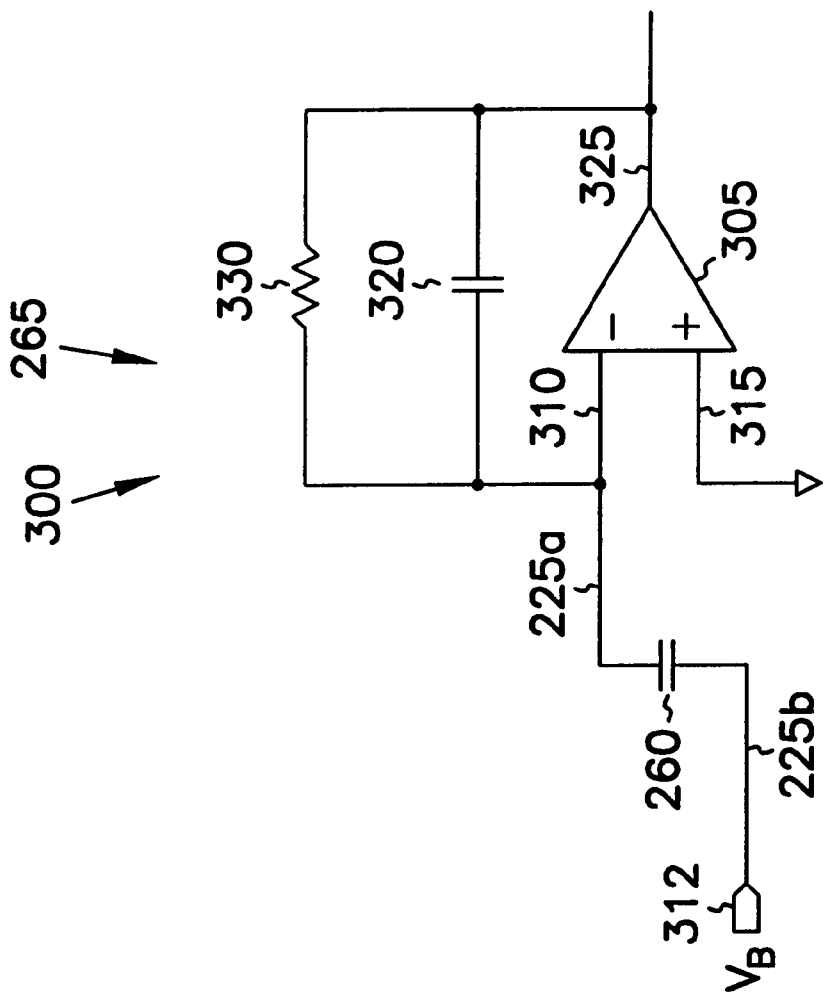
FIG. 3 is a schematic diagram that illustrates generally one charge amplifier embodiment of an input sensor interface circuit.

FIG. 3 is a schematic diagram that illustrates generally, by way of example, but not by way of limitation, one charge amplifier 300 embodiment of interface circuit 265. In the illustrative example of FIG. 3, first and second electrodes of capacitor 260 are accessed by lead wires 255a and 255b. Lead wire 225a is electrically coupled to an inverting input of operational amplifier 305 at node 310. Lead wire 225b is electrically coupled to a bias voltage, $V_B$, at node 312. A noninverting input of operational amplifier 305 at node 315 is electrically coupled to a reference potential, such as a ground voltage, for which noise is minimized. A feedback capacitor 320 is electrically interposed between the inverting input at node 310 and an output of operational amplifier 305 at node 325. A feedback resistor 330 is electrically interposed between the inverting input at node 310 and an output 325 of operational amplifier 305 at node 325. Feedback resistor 330 provides an electrical path for dc biasing the inverting input, at node 310, of operational amplifier 305. This prevents node 310 from floating and provides a virtual ground at the inverting input of operational amplifier 305 at node 310. A dc bias voltage $V_{DC}$ is provided across capacitor 260 as a result of a difference between the virtual ground voltage at the inverting input of operational amplifier 305 at node 310 and the bias voltage $V_B$ at node 312.

In operation, the output of operational amplifier 305 provides at node 325 the charge needed to hold the voltage across capacitor 260 constant, since capacitor 260 is electrically interposed between the bias voltage $V_B$ at node 312 and the virtual ground provided by the inverting input at node 310. The charge provided by the output of operational amplifier 305 at node 325 also flows through feedback capacitor 320. The resulting electrical output signal $v_{325}$ at node 325 is illustrated by Equation 1.

$$v_{325} = \frac{\Delta C_{260}}{C_{320}} V_{DC} \quad (1)$$

In Equation 1, $v_{325}$ is the electrical output signal at the output at node 325 of operational amplifier 305, $\Delta C_{260}$ is the time-varying component of the capacitance value of capacitor 260, $C_{320}$ is the constant capacitance value of feedback capacitor 320, and $V_{DC}$ is the dc bias voltage across capacitor 260.

Figure 4:
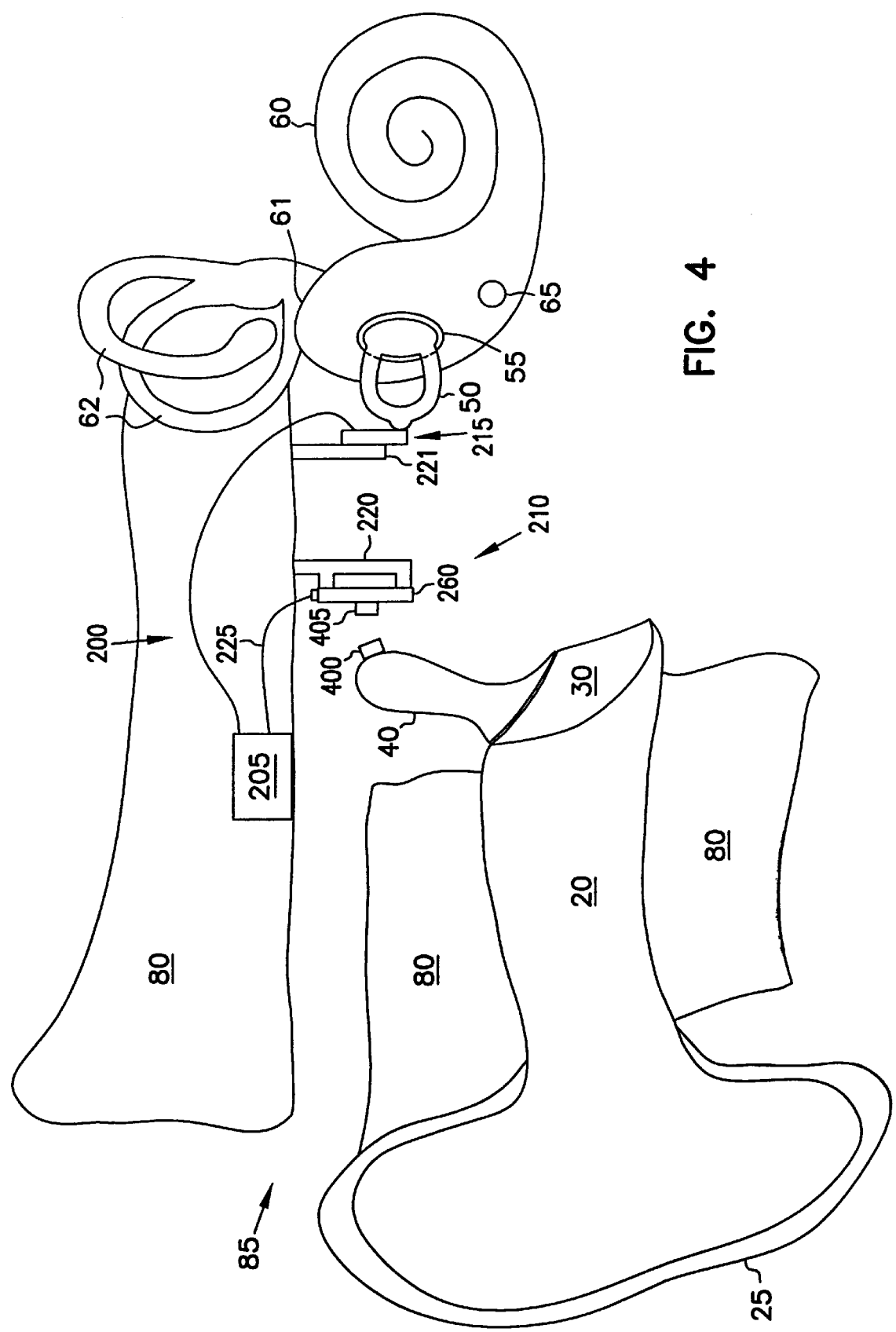
FIG. 4 is a schematic/block diagram illustrating generally a contactless capacitive input sensor alternative to the input sensor of FIG. 2.

FIG. 4 is a schematic/block diagram illustrating generally a portion of another embodiment of a hearing assistance system according to the teachings of the present invention, in which input sensor 210 includes a contactless capacitive sensor for transducing mechanical sound vibrations in the middle ear into an electrical input signal. FIG. 4 also illustrates the use of separate carriers 220 and 221 for input sensor 210 and output stimulator 215, respectively. In FIG. 4, input sensor 210 is magnetically coupled to the auditory element, such as malleus 40, to provide deflective capacitance value variations of capacitor 260, as described below. First and second permanent magnets 400 and 405 are mechanically coupled to the auditory element (e.g., malleus 40) and capacitor 260, respectively, by mechanical, adhesive, or other suitable affixation technique. First and second magnets 400 and 405 are magnetically coupled to each other for providing repulsion therebetween, thereby transmitting the vibrations of the auditory element, such as malleus 40, to capacitor 260. One example of using repulsively coupled permanent magnets is described in co-pending U.S. patent application, entitled CONTACTLESS STIMULATION AND SENSING OF OSSICULAR CHAIN application Ser. No. 08/693,454, filed on Aug. 7, 1996, which disclosure is herein incorporated by reference. The resulting deflective capacitance value variations of capacitor 260 provide an electrical input signal that is coupled to electronics unit 205 through lead wires, illustrated generally by node 225.

Figure 5:
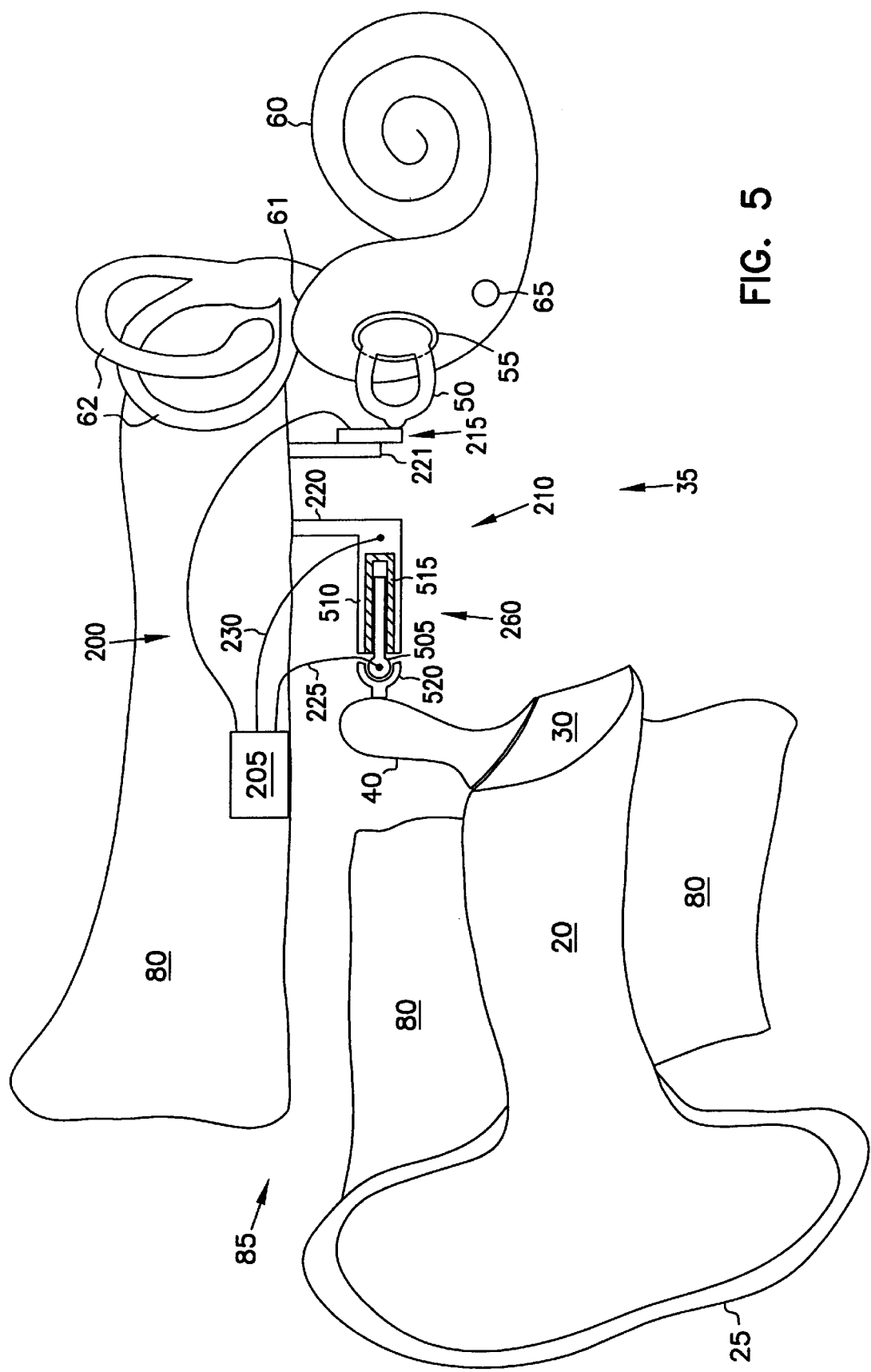
FIG. 5 is a schematic/block diagram illustrating generally a cross-sectional view of a pivotable capacitive input sensor.

FIG. 5 is a schematic/block diagram illustrating generally a cross-sectional view of another embodiment of a hearing assistance system according to the teachings of the present invention. In this embodiment, input sensor 210 includes a capacitive sensor (capacitor) 260 for transducing mechanical sound vibrations in middle ear 35 into an electrical input signal. Capacitor 260 has a first electrode 505 that is directly or indirectly affixed or otherwise mechanically coupled to an auditory element such as malleus 40. Capacitor 260 also includes a second electrode 510 that is disposed within middle ear 35 and separated from first electrode 505 by a dielectric 515. Second electrode 510 is disposed in middle ear 35 such that first electrode 505 is allowed to move with respect to second electrode 510 in response to vibrations of first electrode 505 by the vibrating auditory element.

In one embodiment, for example, second electrode 510 is secured within middle ear 35 by carrier 220. In this embodiment, first electrode 505 is a cylindrical conductor rod that is coaxially received by second electrode 510, which is a hollowed cylindrical conductive sleeve. Dielectric 515 is disposed along the interior sleeve portion of second electrode 510. First electrode 505 moves together with the vibrating auditory element (e.g., malleus 40) thereby changing the capacitance value of capacitor 260. Nodes 225 and 230 electrically connect first and second electrodes 505, 510 to electronics unit 205. In this embodiment, nodes 255, 230 may serve as leads connecting first and second electrodes 505, 510 in a similar manner as leads 225a, 225b, as explained above.

According to another aspect of the invention, first electrode 505 is pivotably mechanically coupled to the vibrating auditory element (e.g., malleus 40). In one embodiment, for example, socket 520 is affixed to malleus 40, such as by deformable wire couplers or any other mechanical fastener, an adhesive, or by any other suitable technique. Socket 520 receives a ball-shaped end of first electrode 505, while the other end of first electrode 505 is coaxially received by the sleeve portion of second electrode 510. This arrangement advantageously allows first electrode 505 to pivot with respect to malleus 40, thereby allowing self-alignment of first electrode 505 with second electrode 510, even if the direction of the vibratory motion of malleus 40 changes as a function of vibration frequency or otherwise. Alternatively, first electrode 505 could be configured as a hollowed cylindrical sleeve and second electrode 510 could be configured as a rod received by and dielectrically separated from the hollowed cylindrical sleeve of first electrode 505 without departing from the scope of the present invention.

Figure 6:
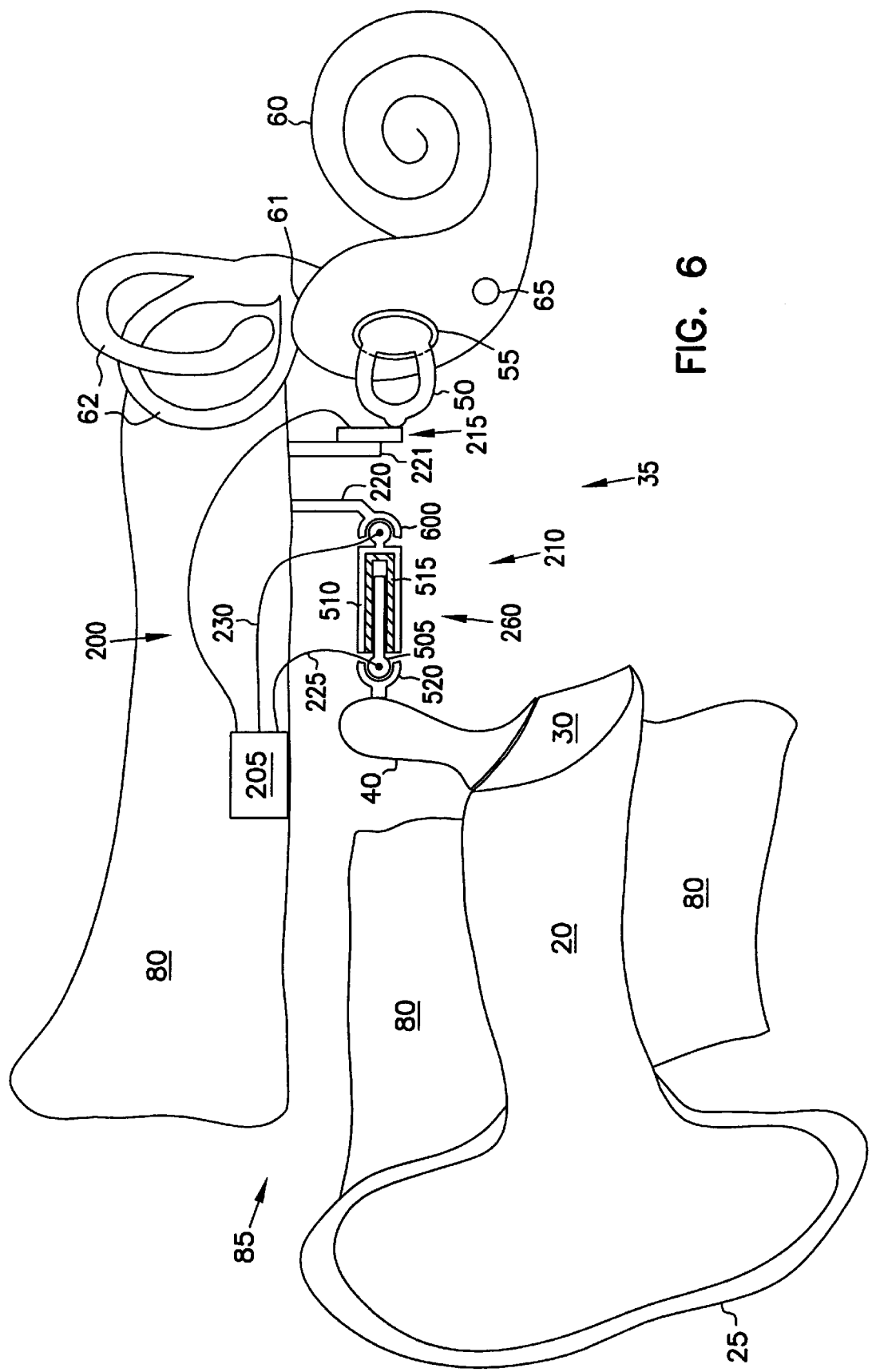
FIG. 6 is a schematic/block diagram, similar to FIG. 5, in which both capacitor electrodes are pivotably secured.

FIG. 6 is a schematic/block diagram illustrating generally a cross-sectional view of a portion of another embodiment of a hearing assistance system according to the teachings of the present invention. The embodiment illustrated in FIG. 6 is similar to the embodiment illustrated in FIG. 5, however, FIG. 6 further provides pivotable coupling of second electrode 510 to carrier 220, thereby providing additional flexibility in the self-alignment of first electrode 505 with second electrode 510. In one embodiment, for example, carrier 220 includes second socket 600 and second electrode 510 includes a ball portion pivotably received by second socket 600. Alternatively, second electrode 510 could include a socket mated with a ball portion of carrier 220. Other techniques of pivotably mating second electrode 510 with carrier 220 and pivotably mating first electrode 505 with socket 520 or the auditory element itself could also be used without departing from the scope of the present invention.

ILLUSTRATIVE EXAMPLE

Figure 7:
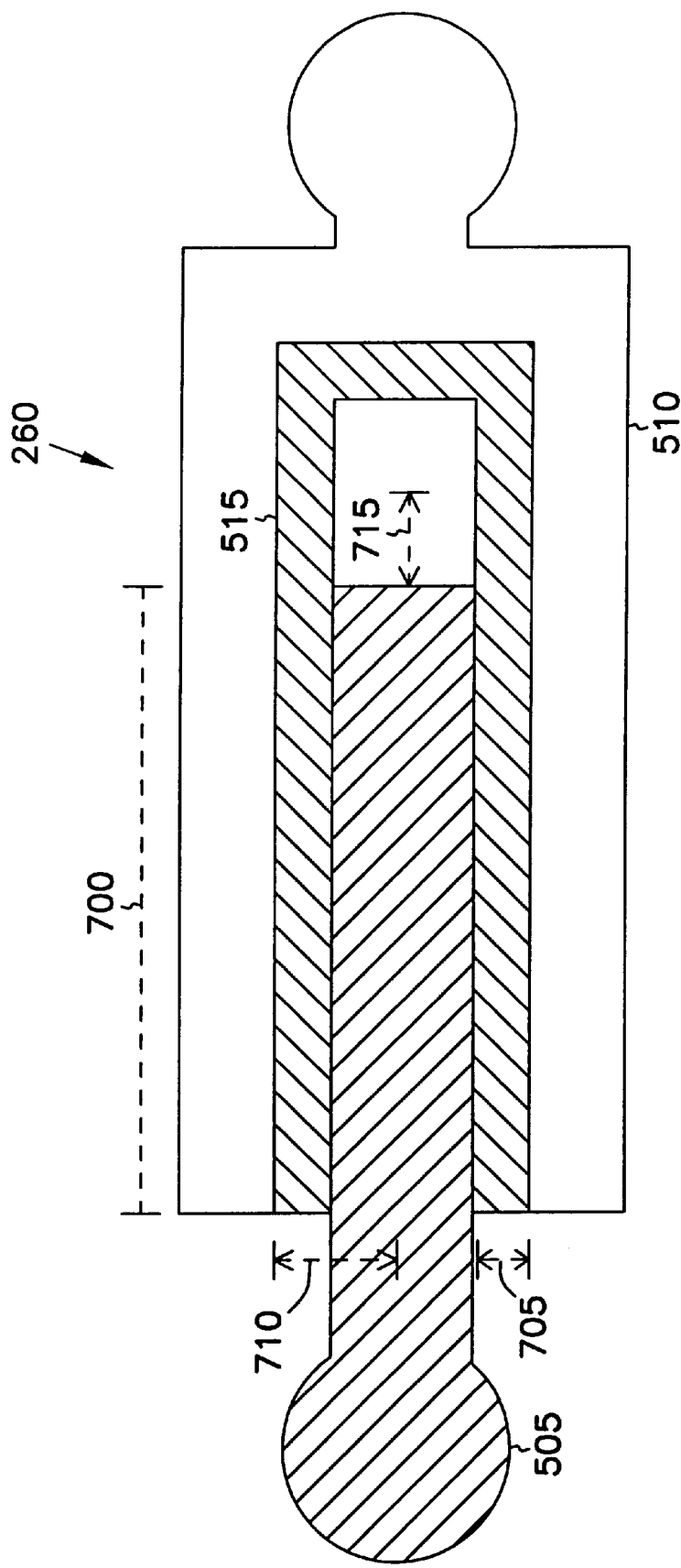
FIG. 7 is a schematic/block diagram illustrating generally a cross-sectional view of a capacitor according to one embodiment of the present invention.

FIG. 7 is a schematic/block diagram illustrating generally, by way of example, but not by way of limitation, a cross-sectional view of capacitor 260, such as illustrated in either of FIG. 5 or FIG. 6. FIG. 7 illustrates generally certain dimensions, including length (L) 700 that first electrode 505 extends within cylindrically hollowed second electrode 510, a thickness (d) 705 by which dielectric 515 separates first electrode 505 from the interior surface of cylindrically hollowed second electrode 510, a radial distance (r) 710 between the inner surface of cylindrically hollowed second electrode 510 and its coaxial center, and a peak-to-peak vibratory amplitude (ΔL) 715 representing a positional change of first electrode 505 with respect to second electrode 510 in response to sound vibrations received from malleus 40 or other auditory element.

The steady-state capacitance value of capacitor 260 is illustrated approximately by Equation 2.

$$C_{260} = \frac{\epsilon 2\pi rL}{d} \quad (2)$$

In Equation 2, $C_{260}$ is the steady-state capacitance value of capacitor 260, $\in$ is the permittivity of dielectric 515, r is the radial distance 710, L is the length 700, and d is the thickness 705 of dielectric 515. In one embodiment, by way of illustrative example, but not by way of limitation, r=3 millimeters, L=2 millimeters, d=0.1 millimeters, and $\in=2\in_o$ (e.g., for dielectric 515 comprising teflon) where $\in_o$=8.85 $(10)^{-14}$ Farads/cm. Such an example embodiment yields a steady-state capacitance value $C_{260}$=6.67 picofarads.

At 100 decibels (dB) sound pressure level (SPL), for example, a typical peak-to-peak vibration amplitude of malleus 40 is approximately ΔL=0.1 micrometers. One voltage amplification embodiment having a dc biasing voltage $V_{DC}$≈2 Volts across capacitor 260 provides an resulting output voltage signal $v_o=(\Delta L/L)V_{DC}$=100 microvolts at 100 dB SPL. One charge amplification embodiment, such as illustrated in FIG. 3, having a dc biasing voltage $V_{DC}$≈2 Volts across capacitor 260 and a feedback capacitor $C_{320}$≈10 picofarads, provides a time-varying capacitance value of capacitor 260 of $\Delta C_{260}$=3.33(10)$^{-4}$ picofarads. An output voltage signal $v_{325}=(\Delta C_{260}/C_{320})V_{DC}$≈66 microvolts is obtained. It should be understood that these examples are provided for illustrative purposes only, and that the particular selection of the above parameters can vary significantly as a matter of design choice.

CONCLUSION

The present invention includes an improved hearing assistance system for sensing sound vibrations of an auditory element in the middle ear and providing a stimulus to an auditory sensory element in response thereto. The present invention provides alternatives to piezoelectric input transducers, which have limited and nonlinear frequency characteristics, potential reliability problems associated with their durability, and mechanical loading that can diminish the gain and frequency sensitivity of the sensed mechanical sound vibrations. Moreover, one aspect of the invention allows sound to pass through the tympanic membrane, incorporating its natural frequency reception characteristics into the sensed vibrations.

It is to be understood that the above description is intended to be illustrative, and not restrictive. Combinations of the above-described embodiments are also included within the scope of the present invention. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An at least partially implantable hearing assistance system, comprising: a capacitive sensor pivotably coupled to an auditory element for receiving vibrations therefrom and varying a capacitance value in response thereto; an electronics unit, operatively interfaced with said capacitive sensor for processing a signal resulting from the varying capacitance value; and an output stimulator, receiving a processed signal based on said varying capacitance value, and providing a resultant stimulus to an auditory element.

2. The system of claim 1, further comprising a programmer adapted for communicative coupling to said electronics unit.

3. The system of claim 2, wherein said programmer is adapted for inductive coupling.

4. The system of claim 2, wherein the programmer is adapted for radio-frequency coupling.

5. The system of claim 2, wherein the programmer is adapted for infrared coupling.

6. The system of claim 2, wherein the programmer is adapted for ultrasonic coupling.

7. The system of claim 2, wherein the programmer is adapted for acoustic coupling.

8. The system of claim 2, wherein the programmer is adapted for transdermal communication.

9. The system of claim 2, further comprising an inductive element.

10. The system of claim 2, wherein the inductive element is a coil.

11. The system of claim 2, wherein the communicative coupling is bi-directional.

12. The programmer of claim 2, further comprising means for adjusting hearing assistance parameters.

13. The programmer of claim 12, wherein said hearing assistance parameters include parameters selected from the group consisting of on/off, standby mode, type of noise filtering, frequency response, volume, gain range, maximum power output, delivery of a test stimulus on demand, and any combination thereof.

14. The programmer of claim 12, wherein at least one of the hearing assistance parameters is adjustable by a patient.

15. The programmer of claim 12, wherein at least one of the hearing assistance parameters is adjustable by a physician.

16. The programmer of claim 2, further comprising means for hearing assistance parameter verification.

17. The programmer of claim 2, further comprising means for hearing assistance parameter diagnosis.

18. A method of transducing a mechanical vibration of an auditory element in a human ear into at least one electrical signal, the method comprising: pivotably coupling a capacitive sensor to the auditory element for receiving vibrations thereby creating capacitance variations; sensing the capacitance variations with an electronics unit, the electronics unit being disposed proximate a patient's middle ear; processing a resulting capacitance variation related electrical signal; and sending the electrical signal to an electrical to vibrational transducer.

19. The method of claim 18, wherein the electronics unit has programmable parameters.

20. The method of claim 19, wherein a programmer is adapted for communicative coupling to the electronics unit.

21. The method of claim 20, wherein the programmer is adapted for electromagnetic coupling to the electronic unit.

22. The method of claim 20, wherein the programmer is adapted for electro-optical coupling to the electronics unit.

23. The method of claim 20, wherein the programmer is adapted for radio frequency coupling to the electronics unit.

24. The method of claim 20, wherein the programmer is adapted for ultrasonic coupling to the electronics unit.

25. The method of claim 20, wherein the programmer is adapted for acoustic coupling to the electronics unit.

26. The method of claim 20, wherein the programmable parameters include parameters selected from the group comprising on/off, standby mode, type of noise filtering, frequency response, volume, gain range, maximum power output, delivery of a test stimulus on demand, and any combination thereof.

27. The method of claim 20, wherein at least one of the parameters is programmable by a patient.

28. The method of claim 20, wherein at least one of the parameters is programmable by a physician.

29. The method of claim 18, further comprising communicatively coupling a programmer to the electronics unit.

30. The method of claim 29, further comprising adjusting programmable parameters of the electronics unit via the programmer.

* * * * *